(12) United States Patent
Niemerg

(10) Patent No.: US 9,556,999 B2
(45) Date of Patent: Jan. 31, 2017

(54) HUNTING TROPHY AND VISUAL DISPLAY PRESENTATION APPARATUS

(71) Applicant: Frank J. Niemerg, Dieterich, IL (US)

(72) Inventor: Frank J. Niemerg, Dieterich, IL (US)

( * ) Notice: Subject to any disclaimer, the term of this patent is extended or adjusted under 35 U.S.C. 154(b) by 0 days.

(21) Appl. No.: 14/539,757

(22) Filed: Nov. 12, 2014

(65) Prior Publication Data

US 2016/0131301 A1    May 12, 2016

(51) Int. Cl.
*A41D 5/00* (2006.01)
*F16M 11/22* (2006.01)
*A01N 1/00* (2006.01)

(52) U.S. Cl.
CPC ............ *F16M 11/22* (2013.01); *A01N 1/00* (2013.01); *A41D 5/006* (2013.01)

(58) Field of Classification Search
CPC ......... G09B 23/36; G09B 23/38; G09B 23/40; A41D 5/006; A01N 1/00; A47F 3/145; F16M 11/22
USPC .................. 248/176.1; 428/16; 434/296, 297
See application file for complete search history.

(56) References Cited

U.S. PATENT DOCUMENTS

| | | | |
|---|---|---|---|
| 550,199 A | 11/1895 | Seymour | |
| 570,245 A | 10/1896 | Bentley | |
| 681,110 A * | 8/1901 | Denton | G09B 23/36 434/297 |
| 1,715,572 A * | 6/1929 | Root | A47B 67/00 206/525 |
| 2,205,686 A * | 6/1940 | Ehrlich | A47F 3/005 119/269 |
| 2,778,487 A * | 1/1957 | Raeburn | B65D 5/22 206/459.5 |
| 3,027,670 A * | 4/1962 | Kramer | A47G 33/004 24/694 |
| 3,269,578 A * | 8/1966 | Lewis | A01G 9/00 119/246 |
| 3,595,727 A * | 7/1971 | Allen | A47G 33/004 248/176.1 |
| 4,464,440 A * | 8/1984 | Dotzman | B44C 5/02 428/16 |

(Continued)

OTHER PUBLICATIONS

Safariworks Taxidermy Sales, The Antler Collection, Trophy Mate Antler Stand—SW1209, http://www.safariworkstaxidermysales.com/Whitetail_antler_display_stand_p/sw1209.htm, May 21, 2014.

(Continued)

*Primary Examiner* — Nkeisha Smith
(74) *Attorney, Agent, or Firm* — Russ Weinzimmer & Associates, PC

(57) ABSTRACT

A hunting trophy presentation apparatus includes a vertical support structure having a plurality of supporting sides disposed so as to provide an enclosure having a first open end and a second open end, a frame connecting the plurality of vertical sides and defining an access opening through which an animal trophy is inserted, and a presentation platform disposed below the frame and providing a mounting surface for an animal trophy. The presentation platform is secured to one of the frame and the vertical support structure, and supports an animal trophy to present the animal trophy above the frame and the vertical support structure. The trophy presentation apparatus also presents a visual display, such as a video or a photograph, attached to the vertical support structure.

11 Claims, 3 Drawing Sheets

(56) References Cited

U.S. PATENT DOCUMENTS

| | | | | |
|---|---|---|---|---|
| 4,717,626 A | * | 1/1988 | Badger | B44C 5/02 428/16 |
| 4,888,251 A | * | 12/1989 | Nakada | A47G 33/00 428/16 |
| 5,058,733 A | * | 10/1991 | Lowe | B65D 85/672 206/281 |
| 5,073,115 A | * | 12/1991 | Howell | A01K 63/003 119/269 |
| 5,135,400 A | * | 8/1992 | Ramey | G09B 23/00 119/246 |
| 5,292,003 A | * | 3/1994 | Baghdassarian | B65D 75/366 206/457 |
| 5,452,846 A | * | 9/1995 | Myers | B65D 5/4262 229/116.3 |
| 5,453,307 A | | 9/1995 | Rezmer | |
| 5,763,102 A | * | 6/1998 | Yau | B44C 3/06 156/59 |
| 6,042,904 A | * | 3/2000 | Greenblat | A47G 33/004 428/13 |
| 6,060,171 A | * | 5/2000 | Greenblat | A47G 33/004 428/13 |
| 6,364,261 B1 | | 4/2002 | Vass, Jr. | |
| 6,458,434 B1 | * | 10/2002 | Coombs, Jr. | B29C 33/304 425/524 |
| 6,581,328 B2 | * | 6/2003 | LaMear | A47G 7/06 206/423 |
| 7,837,038 B2 | * | 11/2010 | Chang | B65D 5/4212 206/459.1 |
| 7,857,266 B2 | | 12/2010 | Damin | |
| 7,987,988 B2 | * | 8/2011 | Johnson | A45C 11/16 206/6.1 |
| 8,172,080 B1 | * | 5/2012 | Schantz | B65D 5/4204 206/278 |
| 8,353,496 B2 | * | 1/2013 | Schwartz | A47G 33/004 248/154 |
| 2005/0006390 A1 | * | 1/2005 | Wang | B65D 45/30 220/326 |
| 2006/0154224 A1 | | 7/2006 | St. Ama | |
| 2007/0039849 A1 | * | 2/2007 | Rodriguez | B65D 5/425 206/457 |
| 2007/0119113 A1 | * | 5/2007 | Keller | E06B 3/4663 52/506.01 |
| 2008/0069977 A1 | | 3/2008 | McAbee | |
| 2009/0152140 A1 | * | 6/2009 | Kim | B65D 85/18 206/293 |
| 2011/0183085 A1 | | 7/2011 | Spiess | |
| 2012/0256061 A1 | * | 10/2012 | Wainionpaa | G09B 23/36 248/200 |
| 2013/0240387 A1 | * | 9/2013 | Pugh | B65D 85/00 206/216 |

OTHER PUBLICATIONS

Skulls Unlimited International, Mounting, European Mount Skull, http://www.skullcleaning.com/, May 21, 2014.

Buck Stumps Inc., Buckstumps Antler Mounting Kit, http://buckstumps.com/Buckstumps, May 21, 2014.

Opticsplanet, Dead Deer True Classic Antler Mount, http://www.opticsplanet.com/doall-out-doors-true-classic-antler-mount.html, May 21, 2014.

* cited by examiner

HUNTING TROPHY AND VISUAL DISPLAY PRESENTATION APPARATUS

FIELD OF THE INVENTION

The present invention relates broadly to displaying hunting trophies, and more specifically relates to trophy presentation apparatus on which antlers or other hunting trophies are mounted.

BACKGROUND OF THE INVENTION

Hunting animals has been a vital activity since man first walked the earth. Trophies from the hunt, being body parts from animals, are displayed with pride by hunters and animal-lovers alike. The taxidermy industry was developed to meet the desire to display such hunting trophies. Traditionally, animal trophies such as antlers, animal heads, and the like, were mounted on plaques attached to a vertical surface such as a wall. However, this approach suffers at least two serious drawbacks. First, mounting a hunting trophy in this manner requires that a person lift the trophy and mounting assembly above their head to attach it to a wall, an operation that normally takes two people standing on ladders. This poses a significant risk of injury to those engaging in this operation, since they can easily fall from the ladder onto a hard floor.

Another shortcoming is that mounting a hunting trophy on a wall presents the trophy at a distance from admirers. The trophy will often be mounted above the height of most people, preventing them from closely examining the hunting trophy.

SUMMARY OF THE INVENTION

One general aspect of the invention is a hunting trophy presentation apparatus including: a first pair of opposing vertical sides; a second pair of opposing vertical sides, the first pair of opposing vertical sides disposed in a perpendicular relationship with the second pair of opposing vertical sides to define a volume of space; a first pair of opposing rails; a second pair of opposing rails, the first pair of opposing rails disposed in a perpendicular relationship with the second pair of opposing rails so as to define a rectangular area, and so as to define a top of the volume of space; and a mounting platform, the mounting platform disposed below the rectangular area.

In some embodiments, the mounting platform is configured to receive a fastener placed in the mounting platform through the rectangular area.

In some embodiments, the apparatus further includes: decorative trim pieces surrounding the rectangular area, and placed on top of the first pair and second pair of opposing rails.

In some embodiments, the apparatus further includes: a video display affixed to one of the vertical sides of the first pair of vertical sides and the second pair of vertical sides. In further embodiments, the video display includes a speaker.

In some embodiments, the apparatus further includes: a photograph presented on at least one of the vertical sides of the first pair of vertical sides and the second pair of vertical sides.

Another general aspect of the invention is a hunting trophy presentation apparatus including: a vertical support structure having a plurality of supporting sides disposed so as to provide an enclosure having a first open end and a second open end; a frame connecting the plurality of supporting sides, and defining an access opening through which an animal trophy can be inserted; and a presentation platform disposed below the frame, and providing a mounting surface for an animal trophy, wherein the presentation platform is secured to one of the frame and the vertical support structure and supports an animal trophy to present the animal trophy above the frame and the vertical support structure.

In some embodiments, the apparatus further includes: a video display affixed to the vertical support structure.

In some embodiments, the apparatus further includes: a speaker.

In some embodiments, the apparatus further includes: at least one photograph attached to the vertical support structure.

Another general aspect of the invention is a hunting trophy presentation apparatus including: a vertical support structure having a plurality of supporting sides disposed so as to provide an enclosure having a first open end and a second open end; a frame connecting the plurality of supporting sides, and defining an access opening through which an animal trophy can be inserted; a presentation platform providing a mounting place for the animal trophy, the presentation platform being secured to one of the frame and the vertical support structure; an animal trophy supported by the presentation platform; and a visual display supported by the vertical support structure.

In some embodiments, the visual display is a video display affixed to the vertical support structure.

In some embodiments, the video display includes a speaker.

In some embodiments, the visual display is a photograph.

In some embodiments, the photograph is presented by a photograph frame attached to the vertical support structure.

BRIEF DESCRIPTION OF THE DRAWINGS

Numerous features and advantages of embodiments of the present invention will be apparent to one skilled in the art upon reading the following detailed description, when considered in conjunction with the accompanying drawings, in which.

DETAILED DESCRIPTION

Figure 1:
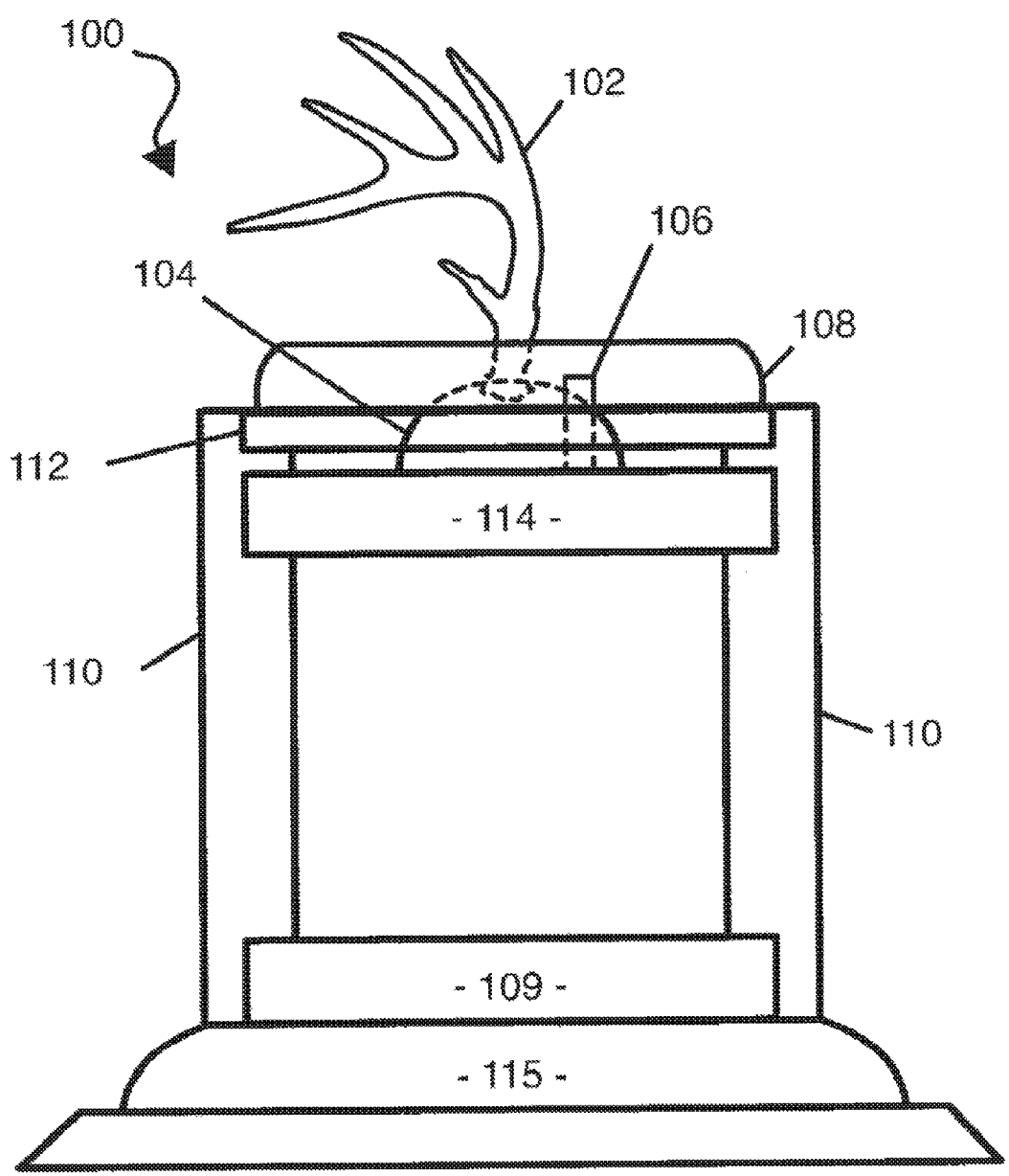
FIG. 1 is a profile view of a hunting trophy presentation apparatus, without its front face.

Directing attention to FIG. 1, there is shown in a profile view a hunting trophy presentation apparatus 100. The hunting trophy presentation apparatus 100 is embodied in a top platform, a subplatform, and supporting sides that allow people to closely examine the hunting trophy presented thereon. As shown in FIG. 1, the hunting trophy presentation apparatus 100 presents hunting trophy 102 still attached to skull base 104 and secured to platform 114 by securing member 106, such as a bolt, screw, or other fastener. Sides 110 are secured by bottom plate 109, and supported by base 115. While the hunting trophy 102 is embodied in a pair of antlers, it is to be understood that a wide variety of hunting trophies can be presented by the hunting trophy presentation apparatus 100. For example, an animal head, a fish, shark jaws, or other desired hunting trophy, can be presented.

Figure 2:
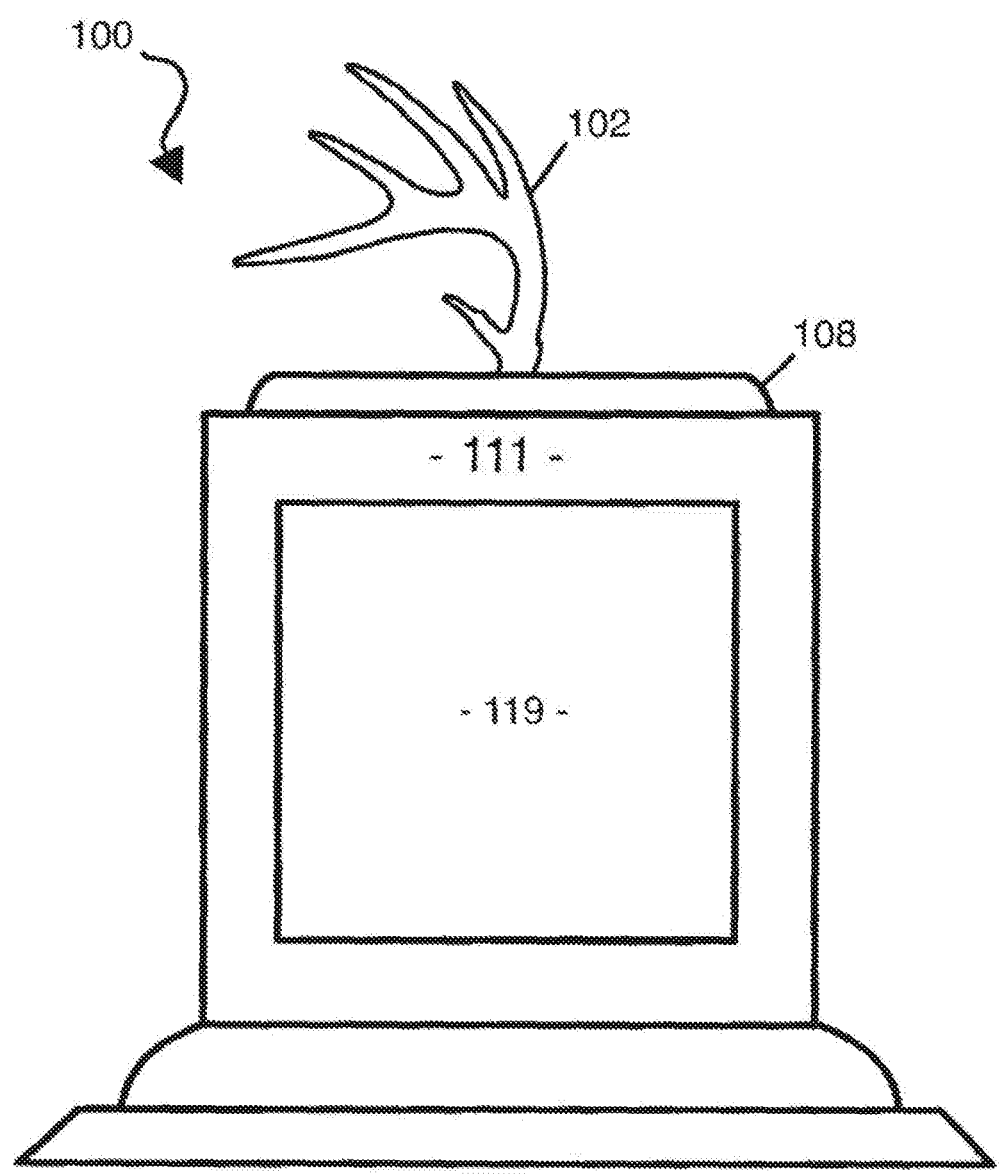
FIG. 2 is a profile view of the hunting trophy presentation apparatus of FIG. 1, with the front face attached, including a display of video, audio, and/or photo.

Directing attention to FIG. 2, sides 110, 111 present smooth surfaces on which a display 119 may be presented. Display 119 can be a flat screen device presenting video and/or audio, or photographs related to the hunting trophy 102 can be displayed. For example, photographs of the type of animal being hunted, the people involved in the hunt, the area in which the hunt took place, or other suitable images can be presented thereon. Similarly, written words can also be displayed in display 119. Display 119 can simply be a frame for a conventional photograph.

Figure 3:
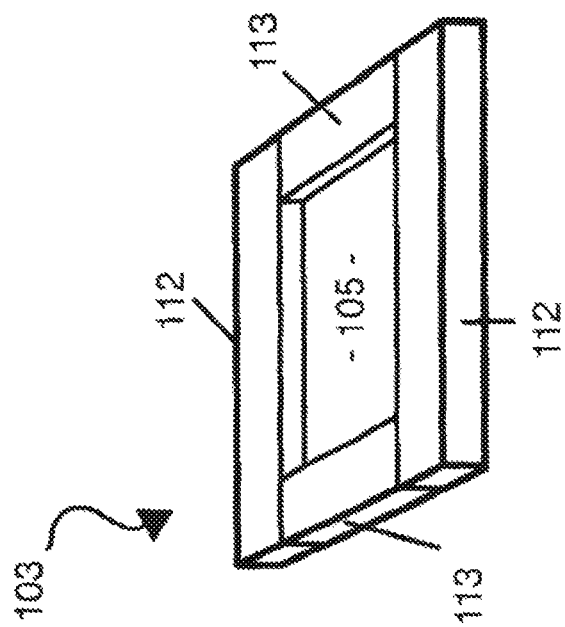
FIG. 3 is a perspective view of the top frame portion of the hunting trophy presentation apparatus of FIG. 1, including two rail pairs in perpendicular relationship, without sides attached.

Directing attention to FIG. 3, hunting trophy presentation apparatus 100 utilizes a top frame 103 defined by a frame comprising two pairs of matched pieces: rail pair 112 and rail pair 113. When secured together, rail pair 112 and rail pair 113 frame a rectangular aperture 105 that receives the hunting trophy 102. Mounting platform 114 is placed beneath aperture 105, and hunting trophy 102 is secured to mounting platform 114 as described above. Decorative trim 108 (FIGS. 1 and 2) may be placed on rail pair 112, 113 to frame aperture 105. Directing attention to FIG. 4, rail pair 112, rail pair 113, and mounting platform 114 are supported by sides 110, 111. Sides 110 are substantially similar in dimension, as are sides 111.

Figure 4:
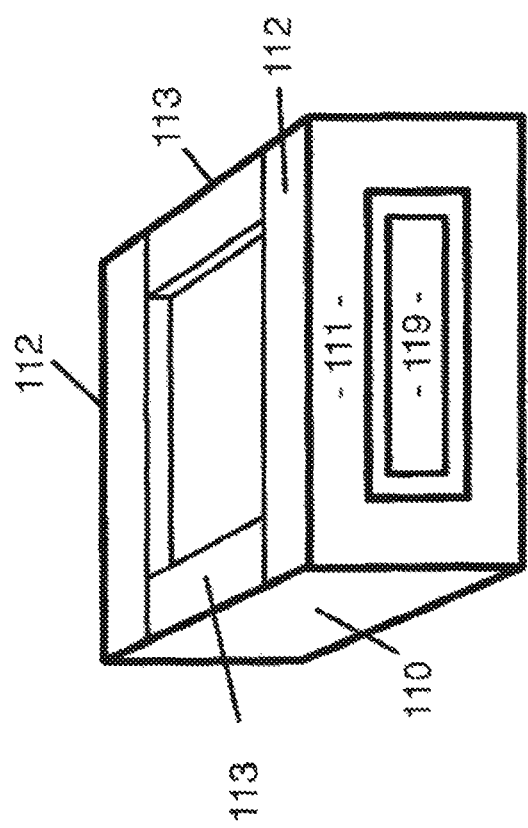
FIG. 4 is a perspective view of the construction of the hunting trophy presentation apparatus of FIG. 1, without the hunting trophy or decorative trim.

Directing attention to FIG. 4, which is similar to FIG. 1, in an embodiment, mounting platform 114 may be adjustable in its vertical position so as to allow a custom depth to accept a wide range of hunting trophies.

While a hunting trophy presentation apparatus has been illustrated and described in detail herein, it is to be understood that numerous modifications can be made to various embodiments of the present invention without departing from the spirit thereof.

What is claimed is:

1. A hunting trophy presentation apparatus comprising:
   a first pair of opposing vertical sides;
   a second pair of opposing vertical sides, the first pair of opposing vertical sides disposed in a perpendicular relationship with the second pair of opposing vertical sides to define a volume of space;
   a first pair of opposing rails;
   a second pair of opposing rails, the first pair of opposing rails disposed in a perpendicular relationship with the second pair of opposing rails so as to define a frame having a rectangular area;
   a mounting platform configured to support at least a portion of a hunted animal, the mounting platform being disposed below the first and second pair of opposing rails to place the mounting platform below the rectangular area thereby providing a recessed framing for the hunted animal;
   a fastener configured to secure the hunted animal to a top of the mounting platform, wherein the mounting platform and frame are spaced from one another so that the hunted animal extends beyond a top of the recessed framing; and
   decorative trim pieces surrounding the rectangular area, and placed on top of the first pair of opposing rails and second pair of opposing rails.

2. The hunting trophy presentation apparatus of claim 1, further comprising:
   a video display affixed to one of the vertical sides of the first pair of opposed vertical sides and the second pair of opposed vertical sides, wherein the video display is configured to display information directly relating to the hunted animal.

3. The hunting trophy presentation apparatus of claim 2, wherein the video display includes a speaker.

4. The hunting trophy presentation apparatus of claim 2, wherein the video display is configured to display information relating to hunted animal type, people involved in hunting the hunted animal, and/or a geographic area in which the hunted animal was hunted.

5. The hunting trophy presentation apparatus of claim 1, further comprising:
   a photograph presented on at least one of the vertical sides of the first pair of opposed vertical sides and the second pair of opposed vertical sides.

6. A hunting trophy presentation apparatus comprising:
   a vertical support structure having a plurality of supporting sides disposed so as to provide an enclosure having a top open end;
   a frame connecting the plurality of supporting sides at the top open end, and defining an access opening through which at least a portion of a hunted animal can be inserted;
   a presentation platform providing a mounting surface at which the hunted animal is mounted by a fastener, wherein the fastener is configured to secure the hunted animal to a top of the mounting surface, the presentation platform being secured to one of the frame and the vertical support structure;
   at least a portion of a hunted animal supported by the presentation platform, wherein the mounting surface and top end of the frame being spaced from one another to present the hunted animal so that the hunted animal extends above the frame and the vertical support structure; and
   a visual display supported by the vertical support structure, wherein the visual display is configured to display information directly relating to the hunted animal.

7. The hunting trophy presentation apparatus of claim 6, wherein the visual display is a video display affixed to the vertical support structure.

8. The hunting trophy presentation apparatus of claim 7, wherein the video display includes a speaker.

9. The hunting trophy presentation apparatus of claim 7, wherein the video display is configured to display information relating to hunted animal type, people involved in hunting the hunted animal, and/or a geographic area in which the hunted animal was hunted.

10. The hunting trophy presentation apparatus of claim 6, wherein the visual display is a photograph.

11. The hunting trophy presentation apparatus of claim 10, wherein the photograph is presented by a photograph frame attached to the vertical support structure.

* * * * *